(12) United States Patent
Ito et al.

(10) Patent No.: US 7,897,395 B2
(45) Date of Patent: Mar. 1, 2011

(54) MICROINJECTION APPARATUS, TRAP PLATE AND MICROINJECTION METHOD

(75) Inventors: Akio Ito, Kawasaki (JP); Akihiko Yabuki, Kawasaki (JP); Daisuke Uchida, Kawasaki (JP); Satoru Sakai, Kawasaki (JP); Sachihiro Youoku, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 228 days.

(21) Appl. No.: 12/081,994

(22) Filed: Apr. 24, 2008

(65) Prior Publication Data

US 2008/0268540 A1    Oct. 30, 2008

(30) Foreign Application Priority Data

Apr. 27, 2007    (JP) .............................. 2007-119924

(51) Int. Cl.
*C12N 15/66*    (2006.01)
(52) U.S. Cl. ................... 435/455; 435/470; 435/471; 435/285.1; 435/286.4
(58) Field of Classification Search ................ None
See application file for complete search history.

(56) References Cited

U.S. PATENT DOCUMENTS

| | | | |
|---|---|---|---|
| 4,729,949 A | 3/1988 | Weinreb et al. |
| 4,895,805 A | 1/1990 | Sato et al. |
| 4,907,158 A | 3/1990 | Kettler et al. |
| 6,537,801 B1 | 3/2003 | Ida et al. |
| 6,593,129 B1 | 7/2003 | Takeshita et al. |
| 2003/0152255 A1 | 8/2003 | Kira et al. |
| 2005/0214932 A1 | 9/2005 | Sasaki et al. |
| 2005/0250197 A1 | 11/2005 | Ando et al. |
| 2006/0024812 A1 | 2/2006 | Youoku et al. |
| 2008/0206828 A1 | 8/2008 | Kotera et al. |

FOREIGN PATENT DOCUMENTS

| | | |
|---|---|---|
| DE | 3829028 | 3/1989 |
| EP | 0 292 899 | 5/1988 |
| EP | 0311059 | 4/1989 |
| EP | 1182250 | 2/2002 |
| EP | 1479759 | 11/2004 |
| EP | 1595941 | 11/2005 |
| EP | 1683855 | 7/2006 |
| JP | 2624719 | 4/1997 |
| JP | 10-127267 | 5/1998 |
| JP | 2000-23657 | 1/2000 |
| JP | 2002-65240 | 3/2002 |
| JP | 2002-526773 | 8/2002 |
| JP | 2003- 307518 | 10/2003 |
| JP | 2005-318851 | 11/2005 |
| WO | WO 91/05519 | 5/1991 |
| WO | 2006/098430 | 9/2006 |

OTHER PUBLICATIONS

Extended European Search Report dated Jul. 28, 2008 in related European Application No. 08103729.3.
Extended European Search Report dated Oct. 8, 2008 in related European Application No. 08157325.5.
U.S. Appl. No. 12/155,003, filed May 28, 2008, Akio Ito et al., Fujitsu Limited.
Patent Abstracts of Japan, Publication No. 10-127267, Published May 19, 1998.
European Search Report dated Jan. 15, 2007 in Application No. 05 25 1126.
Patent Abstracts of Japan, Publication No. 10-127267, Published May 19, 1998.
Office Action in U.S. Appl. No. 12/155,003 dated Jun. 18, 2010.
Office Action in U.S. Appl. No. 11/066,296 dated Oct. 7, 2008.
Office Action in U.S. Appl. No. 11/066,296 dated Jul. 28, 2009.
Office Action in U.S. Appl. No. 11/066,296 dated Dec. 4, 2009.
European Search Report dated Jan. 15, 2007 in Application No. 05 25 1126.

*Primary Examiner*—James S Ketter
(74) *Attorney, Agent, or Firm*—Staas & Halsey LLP

(57) ABSTRACT

A microinjection apparatus has a trap plate which traps at least one cell, so as to fix a position thereof, a capillary needle which injects a substance into the cell trapped by the trap plate, a movement mechanism portion which thrusts a distal end of the capillary needle onto a in a lengthwise direction of the needle, and which withdraws the capillary needle in the lengthwise direction thereof, and a discharge control portion which discharges the substance from the distal end of the capillary needle, when the capillary needle has been withdrawn to a predetermined position by the movement mechanism portion.

14 Claims, 16 Drawing Sheets

NEGATIVE PRESSURE

MICROINJECTION APPARATUS, TRAP PLATE AND MICROINJECTION METHOD

CROSS-REFERENCE TO RELATED APPLICATION

This application claims the benefit under 35 U.S.C. §119 of Japanese Application No. 2007-119924, filed Apr. 27, 2007, which is incorporated herein by reference.

BACKGROUND

The present invention relates to a microinjection apparatus, a trap plate and a microinjection method. More particularly, it relates to a microinjection apparatus, a trap plate and a microinjection method which can reliably inject a chemical agent into a cell and which can protect the distal end of a capillary needle.

In recent years, researches have been able to alter the genetic information of cells by injecting genes directly into the cells. Using this technique, the roles of the genes are clarified, and a tailor-made medical treatment, for example, a gene treatment suited to the genetic characteristics of an individual becomes possible.

As schemes for injecting the gene into the cell, there have been proposed an electrical method (eletroporation), a chemical method (lipofection), a biological method (vector method), a mechanical method (microinjection), an optical method (laser injection), etc. Disadvantageously, however, the electrical scheme damages the cell heavily because a cell membrane is broken by causing a large current to flow through the cell, the chemical scheme has an inferior efficiency because introducible genes are limited, and the biological method is incapable of ensuring safety because all materials cannot be introduced into the cell. On the other hand, the mechanical method appears to be the method which is the safest and which has the highest efficiency.

In the microinjection, as shown in FIG. 13, a capillary needle 10 is automatically moved to the position of a cell C so as to directly inject a chemical agent. On this occasion, the position of the cell C needs to be fixed within a laboratory dish 20 in order that the capillary needle 10 may move precisely to the position of the cell C. In FIG. 13, therefore, a trap plate 30 provided with a plurality of penetrating apertures is mounted in the laboratory dish 20, and the side of the trap plate 30 near to the bottom of the laboratory dish 20 is held at a negative pressure, whereby the cell C is sucked onto the penetrating aperture of the trap plate 30.

That is, in FIG. 13, the laboratory dish 20 is filled with a buffer liquid, and the trap plate 30 and the cell C are immersed in the buffer liquid. In addition, the buffer liquid is sucked from the bottom of the laboratory dish 20, whereby the side of the trap plate 30 near to the bottom of the laboratory dish 20 is brought to the negative pressure, and the cell C is sucked onto the penetrating aperture provided in the trap plate 30. Thus, the position of the cell C is fixed at the position of the penetrating aperture of the trap plate 30. When the coordinates of the penetrating aperture are stored beforehand, the capillary needle 10 can be moved precisely to the position of the cell C.

Meanwhile, in the case where the position of the cell C is fixed by the suction, it is difficult to appropriately adjust the relationship between the size of the cell and the size of the penetrating aperture. More specifically, as shown in FIG. 14 by way of example, in a case where the penetrating aperture of the trap plate 30 is excessively large relative to the size of the cell C, the cell C itself might be drawn into the penetrating aperture by the suction. Besides, as shown in FIG. 15 by way of example, in a case where the penetrating aperture of the trap plate 30 is excessively small relative to the size of the cell C, the position of the cell C cannot be reliably fixed, and the cell C sometimes undesirably moves when touched by the capillary needle 10.

In this regard, as described in Japanese laid-open Patent Publication No. 2005-318851, a penetrating aperture of small diameter is provided in a trap plate, while a recess of large diameter is provided around the penetrating aperture. That is, in the trap plate of Japanese laid-open patent publication No. 2005-318851, the penetrating aperture is provided at the center of the circular flat recess which is lower in level than the surroundings. According to such a trap plate, a cell is adsorbed on the trap plate by suction from the penetrating aperture, while at the same time, the position of the cell is reliably fixed by the recess.

In general, however, the cell membrane of a cell is highly flexible, and it is difficult to break even when a capillary needle is thrust thereagainst. This poses the problem that the reliable injection of a chemical agent into the cell is difficult. That is, as shown in FIG. 16 by way of example, even when the cell is reliably fixed by the circular recess and the penetrating aperture, the upside cell membrane sometimes stretches into the cell with the thrust of the capillary needle, so that the distal end of the capillary needle fails to enter the interior of the cell. In addition, even when the chemical agent is discharged from the distal end of the capillary needle in this state, it is not injected into the cell, and the microinjection ends in failure.

Besides, when the thrust magnitude of the capillary needle is increased to the extent that the upside cell membrane of the cell touches the downside cell membrane thereof as shown in FIG. 16, it is expected that the upside cell membrane will break, and that the distal end of the capillary needle will enter the interior of the cell. In this case, however, the capillary-needle distal end substantially abuts the downside cell membrane, and hence, a space sufficient for injecting the chemical agent thereinto is not defined between the capillary-needle distal end and the downside cell membrane.

Further, when the thrust magnitude of the capillary needle is excessively increased, the distal end of the capillary needle might pierce also the downside cell membrane, and the chemical agent might be discharged outside the cell. Moreover, the distal end of the capillary needle sometimes touches the trap plate and is then damaged. Especially in the microinjection, the cell to be handled has a size on the order of several μm to several tens μm, so that the movement of the capillary needle becomes minute. Therefore, even in case of an error of 1 to 2 μm by way of example, the capillary needle sometimes touches the trap plate, and it is likely to be damaged.

The present invention has been made in view of such drawbacks, and it has for its object to provide a microinjection apparatus, a trap plate and a microinjection method which can reliably inject a chemical agent into a cell and which can protect the distal end of a capillary needle.

SUMMARY

In accordance with an aspect of a microinjection apparatus, the apparatus has a trap plate which traps at least one cell, a capillary needle which injects a substance into the cell trapped by the trap plate, a movement mechanism portion which thrusts or moves the capillary needle, and a discharge control portion which discharges the substance from a distal end of the capillary needle when the capillary needle has been moved to a predetermined position by the movement mechanism portion.

DETAILED DESCRIPTION OF THE EMBODIMENTS

Embodiments of the present invention will now be described in detail with reference to the drawings.

In general, a chemical agent is discharged after withdrawal of a capillary needle is started subsequent to the thrust of the capillary needle to the maximum, and a trap plate is provided with a depression near an extension line of the capillary needle in the lengthwise direction thereof, thereby to prevent the distal end of the capillary needle from touching the trap plate.

Figure 1:
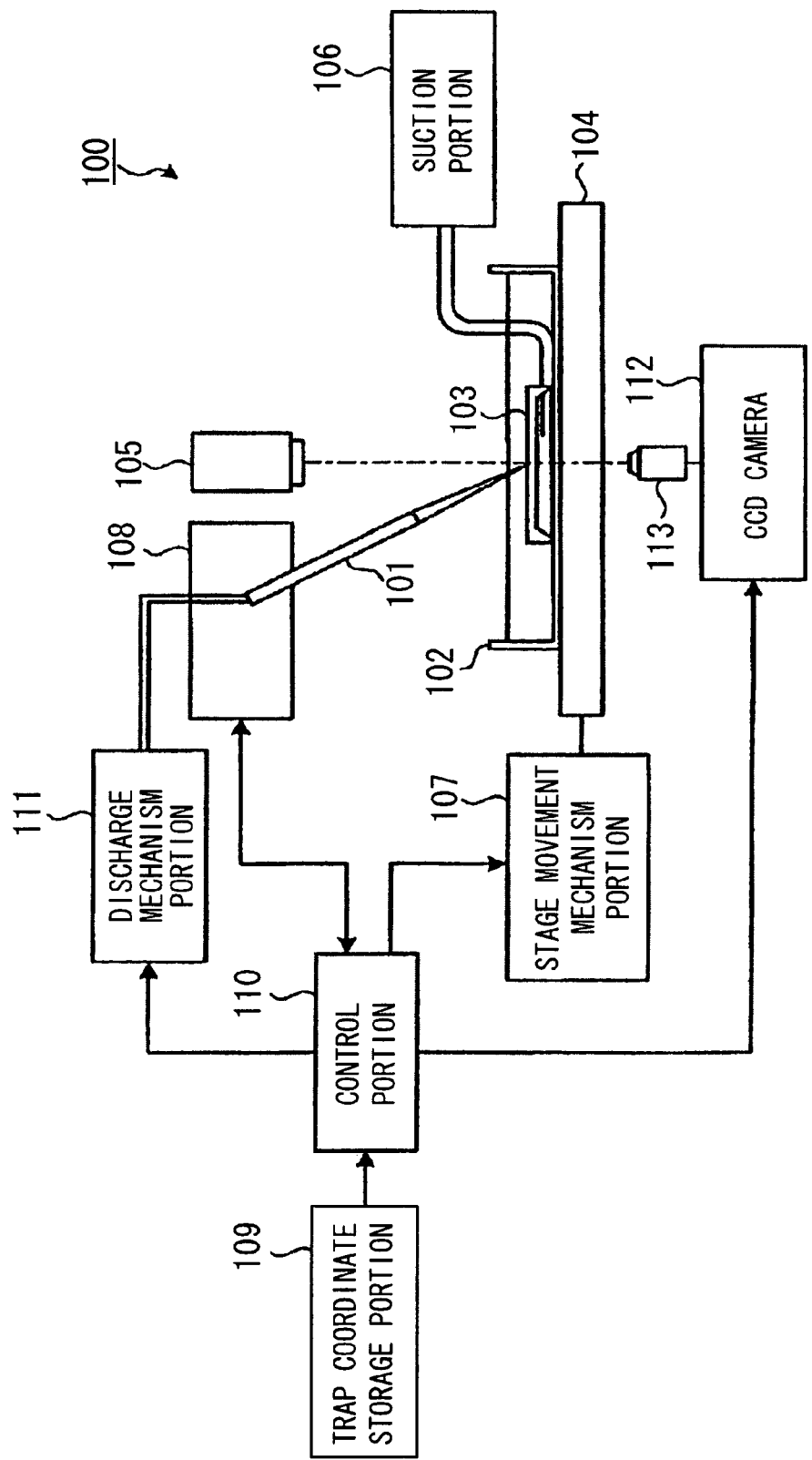
FIG. 1 is a schematic block diagram showing the configuration of an automatic microinjection apparatus according to an embodiment of the present invention.

FIG. 1 shows the configuration of an automatic microinjection apparatus 100 according to an embodiment of the invention. The automatic microinjection apparatus 100 includes a capillary needle 101, a laboratory dish 102, a trap plate 103, a stage 104, an illuminator 105, a suction portion 106, a stage movement mechanism portion 107, a capillary-needle movement mechanism portion 108, a trap coordinate storage portion 109, a control portion 110, a discharge mechanism portion 111, a CCD (Charge Coupled Device) camera 112, and an inverted microscope 113.

The capillary needle 101 is attached to the capillary-needle movement mechanism portion 108, and it is moved on a horizontal surface and is thrust and pulled up in the lengthwise direction thereof. In addition, the capillary needle 101 discharges a chemical agent held therein, when a discharge pressure is added from the discharge mechanism portion 111.

The laboratory dish 102 is a substantially cylindrical vessel in which the diameter of the bottom thereof is large relative to the height thereof, and it is filled with a buffer liquid in which cells can survive. This laboratory dish 102 is placed on the stage 104, and it is moved on a horizontal surface together with the stage 104.

The trap plate 103 is accommodated centrally of the laboratory dish 102, and it traps the cells in the buffer liquid, at the positions of trap apertures provided in a surface thereof parallel to the bottom of the laboratory dish 102. Sealing is performed between the trap plate 103 and the bottom of the laboratory dish 102, with a side of the trap plate 103 near to the bottom of the laboratory dish 102 and the upper side of the trap plate 103 are continuous through only the trap apertures of the trap plate 103. A more detailed explanation of the shape and function of the trap plate 103 will be explained later.

The stage 104 is fixed to the stage movement mechanism portion 107, and it can receive the laboratory dish 102 on its upper surface. In addition, the stage 104 is moved on a horizontal surface by the control of the stage movement mechanism portion 107 in order that the cell which is trapped by the trap plate 103 and which is a subject for injection may be located perpendicularly below the illuminator 105 and perpendicularly above the lens of the inverted microscope 113. Incidentally, the stage 104 is fabricated of a transparent material or is provided centrally with a photographing hole corresponding to the trap plate 103, in order that the CCD camera 112 can photograph the cell on the trap plate 103.

The illuminator 105 is a light source which illuminates the cell trapped on the trap plate 103, and it is disposed perpendicularly above the lens of the inverted microscope 113.

The suction portion 106 sucks the buffer liquid from the side of the trap plate 103 near to the bottom of the laboratory dish 102 to create a negative pressure state.

The stage movement mechanism portion 107 moves the stage 104 on the horizontal surface in compliance with an instruction from the control portion 110. More particularly, the stage movement mechanism portion 107 moves the stage 104 in order that the coordinates of the trap aperture of the trap plate 103 on which the cell is trapped may be located perpendicularly below the illuminator 105 and perpendicularly above the lens of the inverted microscope 113.

The capillary-needle movement mechanism portion 108 moves the capillary needle 101 on the horizontal surface in order that the distal end of the capillary needle 101 in the injection mode may be located perpendicularly below the illuminator 105 and perpendicularly above the lens of the inverted microscope 113. Besides, the capillary-needle movement mechanism portion 108 thrusts the capillary needle 101 onto the distal end side thereof in the lengthwise direction thereof after the completion of the movement of the capillary needle 101 on the horizontal surface, and it thereafter pulls up the capillary needle 101 in the lengthwise direction thereof. On this occasion, the capillary-needle movement mechanism portion 108 notifies the central portion 110 of the location of the capillary needle 101 in the lengthwise direction.

The trap coordinate storage portion 109 stores the coordinates of the trap apertures which are provided in the trap plate 103 within the laboratory dish 102. In other words, the trap coordinate storage portion 109 stores the trap coordinates at which the cells are trapped, beforehand.

The control portion 110 retrieves the coordinates of the trap aperture from the trap coordinate storage portion 109, and instructs the stage movement mechanism portion 107 to locate the retrieved coordinates perpendicularly below the illuminator 105 and perpendicularly above the lens of the inverted microscope 113. Besides, when the position of the stage 104 has been adjusted, the control portion 110 instructs the capillary-needle movement mechanism portion 108 to finely adjust the position of the capillary needle 101.

Further, the control portion 110 receives the notification of the displacement of the capillary needle 101 in the lengthwise direction thereof from the capillary-needle movement mechanism portion 108. Thus, the control portion 110 instructs the discharge mechanism portion 111 to discharge the chemical agent when the capillary needle 101 has been pulled up to a predetermined position after the thrust thereof to the maximum. That is, the control portion 110 instructs the discharge mechanism portion 111 to discharge the chemical agent when the capillary needle 101 has come nearest to the trap plate 103, and thereafter, a height from the trap plate 103 to the distal end of the capillary needle 101 has arrived at a predetermined value.

When instructed to discharge the chemical agent by the control portion 110, the discharge mechanism portion 111 adds a discharge pressure to the interior of the capillary needle 101 so as to discharge the chemical agent from the distal end of the capillary needle 101.

The CCD camera 112 photographs the injection of the chemical agent into the cell which is trapped on the trap plate 103 and whose image is enlarged by the inverted microscope 113. After the injection of the chemical agent, the CCD camera 112 photographs changes which have occurred in the cell.

The inverted microscope 113 is disposed at a position at which the image of a place perpendicularly below the illuminator 105 can be enlarged, and it enlarges the images of the vicinity of the distal end of the capillary needle 101 and the cell trapped on the trap plate 103.

Figure 2:
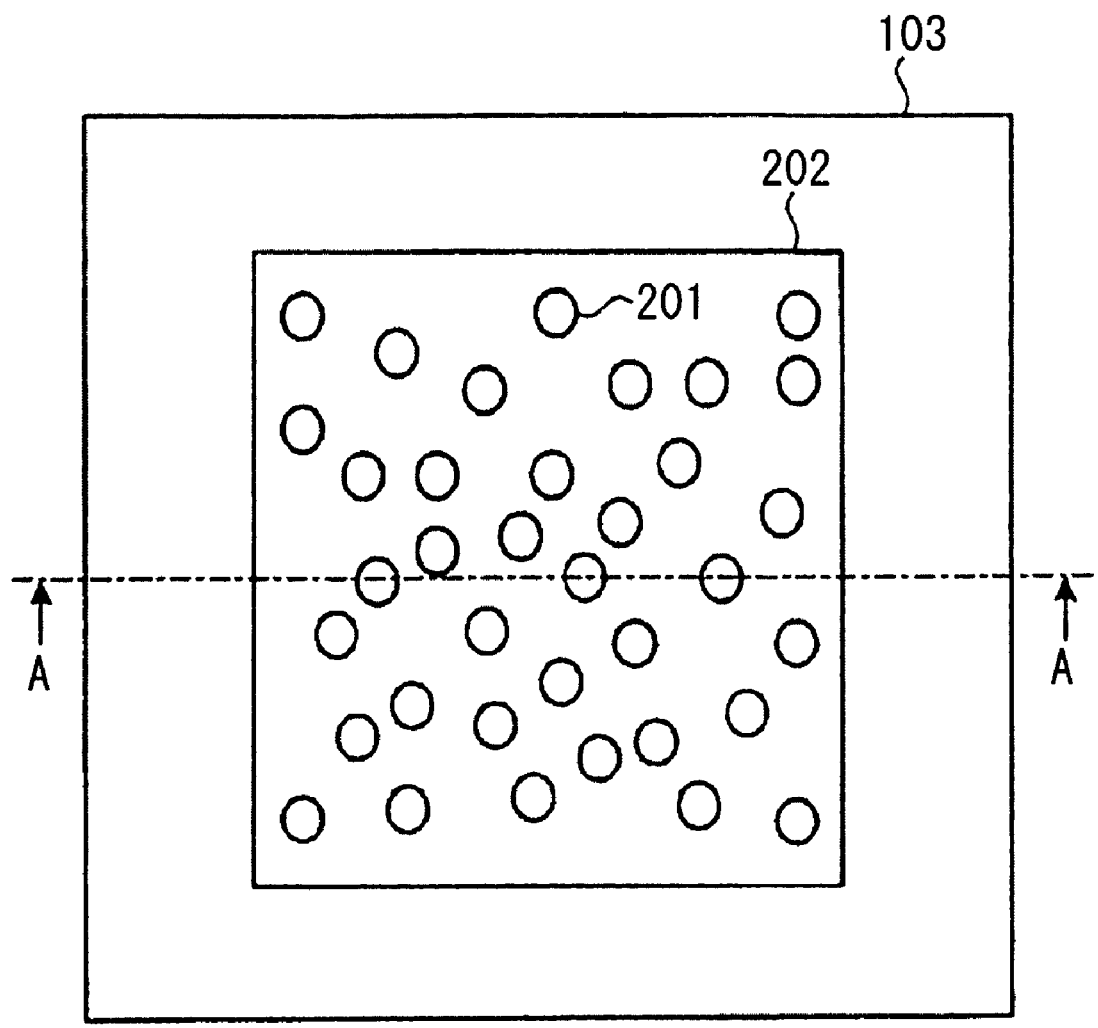
FIG. 2 is a plan view of a trap plate according to an embodiment.

FIG. 2 is a plan view of the trap plate 103 according to the embodiment. As shown in the figure, a plurality of trap apertures 201 is formed in the central flat part 202 of the trap plate 103. The trap apertures 201 may be regularly arrayed in the flat part 202, but they are shown random in FIG. 2, whereby cracks are difficult to form in the flat part 202, and the strength thereof can be ensured. In this regard, one of the sides of the trap plate 103 with the flat part 202 interposed therebetween (that is, the side near to the bottom of the laboratory dish 102) receives the negative pressure state, so that the strength of the flat part 202 needs to be ensured to some extent.

Besides, the coordinates of the trap apertures 201 in the flat part 202 are stored in the trap coordinate storage portion 109 beforehand. Accordingly, the cell trapped on a trap aperture 201 can be set as the subject for the injection, by moving the stage 104 on the horizontal surface in order that the coordinates of that trap aperture 201 may be located perpendicularly below the illuminator 105 and perpendicularly above the lens of the inverted microscope 113. As will be described later, the diameter of the trap aperture 201 should desirably be about 70% to 80% of the diameter of the cell being the subject for the injection. Thus, when the diameter of the cell is 16 μm or so by way of example, the diameter of the trap aperture 201 should desirably be 12 μm or so.

Figure 3:
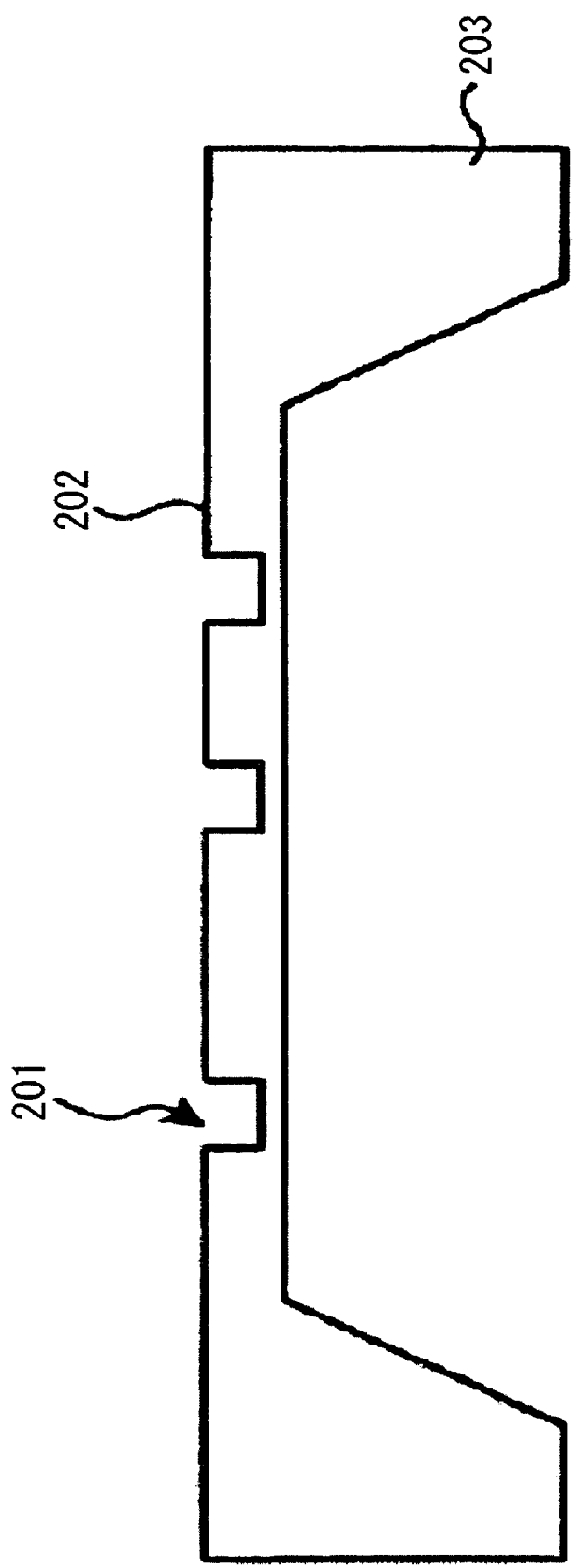
FIG. 3 is a sectional view of the trap plate according to the embodiment.

FIG. 3 is a sectional view showing a section taken along line A-A in FIG. 2. As shown in FIG. 3, the trap plate 103 is formed with the leg 203 at the periphery of the flat part 202, and the leg 203 is tightly secured to the bottom of the laboratory dish 102, so that only the penetrating apertures provided in the trap apertures 201 serve as the passages of the surrounding buffer liquid. More specifically, the penetrating apertures are provided in the bottoms of the trap apertures 201 though not shown in FIG. 3, and the lower side of the flat part 202 undergoes the negative pressure, whereby the buffer liquid on the upper side of the flat part 202 is sucked onto the lower side of the flat part 202 with the passages being the penetrating apertures which are provided in the bottoms of the trap apertures 201. On this occasion, the cell in the buffer liquid is adsorbed on the trap aperture 201 together with the buffer liquid, and it is trapped by the trap aperture 201.

A depth from the flat part 202 to the bottom of the trap aperture 201 needs to be a depth capable of reliably fixing the cell, and it should desirably be about 3 to 4 μm when the diameter of the cell is about 16 μm by way of example. Accordingly, the thickness of the flat part 202 is required to be greater than the depth of the trap aperture 201, and it is set at about 10 μm by way of example.

Figure 4:
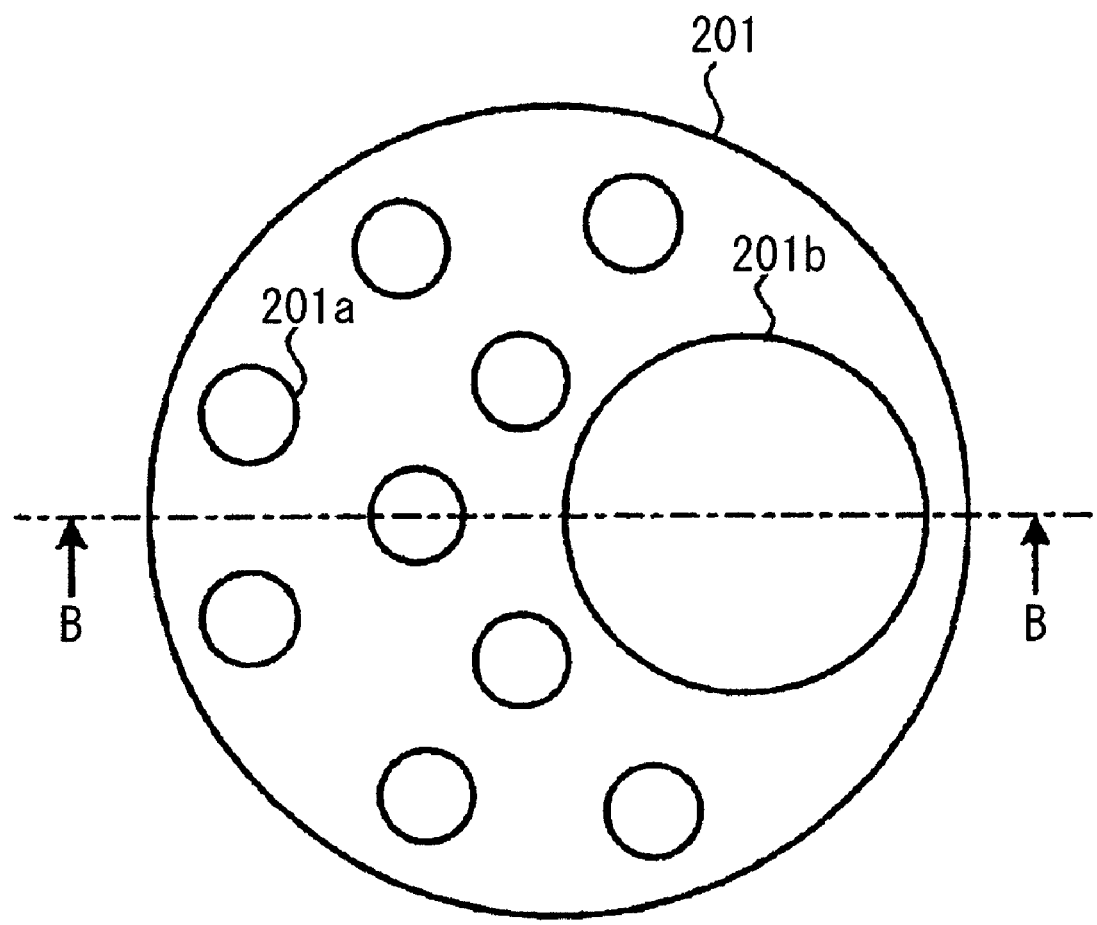
FIG. 4 is a plan view of trap apertures according to an embodiment.

FIG. 4 is a plan view of the trap aperture 201 according to this embodiment. As shown in the figure, the plurality of penetrating apertures 201a is formed in the trap aperture 201, and a circular recess 201b is provided in the trap aperture. Incidentally, only one penetrating aperture 201a may be formed in the trap aperture 201, and even in the case of forming the plurality of penetrating apertures 201a in the trap aperture 201, the arrangement thereof is not limited to that shown in FIG. 4.

The diameter of each penetrating aperture 201a is sufficiently small as compared with the diameter of the cell to-be-trapped, and it is about 1 to 2 μm by way of example. Alternatively, the diameter of the penetrating aperture 201a may well be set at about 10% to 20% with respect to the diameter of the cell. The penetrating apertures 201a serve as the passages of the buffer liquid and adsorb the cells when the lower sides of the trap apertures 201 are in the negative pressure state. In this embodiment, the plurality of penetrating apertures 201a is formed in one trap aperture 201, thereby to enlarge an adsorptive force for the cell.

The recess 201b is formed by depressing a circular part which centers round the intersection point between the bottom of the trap aperture 201 and the extension line of the capillary needle 101 in the lengthwise direction thereof. More specifically, in this embodiment, as shown in FIG. 1, the lengthwise direction of the capillary needle 101 is set so as to define a predetermined angle relative to a vertical direction, so that the recess 201b is formed at a position deviating from the center of the trap aperture 201. However, if the lengthwise direction of the capillary needle 101 coincides with the vertical direction, the recess 201b is formed centrally of the trap aperture 201.

In thrusting the capillary needle 101 by the capillary-needle movement mechanism portion 108, the recess 201b functions as a place of refuge in the case where a thrust magnitude becomes excessive due to an error. Accordingly, the diameter of the recess 201b is determined in accordance with that extent of the bottom of the trap aperture 201 with which the distal end of the capillary needle 101 can come into contact, and it should desirably be set at about 3 to 4 μm by way of example. Owing to the provision of the recess 201b, even in the case where the thrust magnitude of the capillary needle 101 becomes excessive, the distal end of the capillary needle 101 is confined within the extent of the recess 201b, it does not touch the trap plate 103 proper, so that the trap plate 103 can be prevented from damaging the needle 101.

Figure 5:
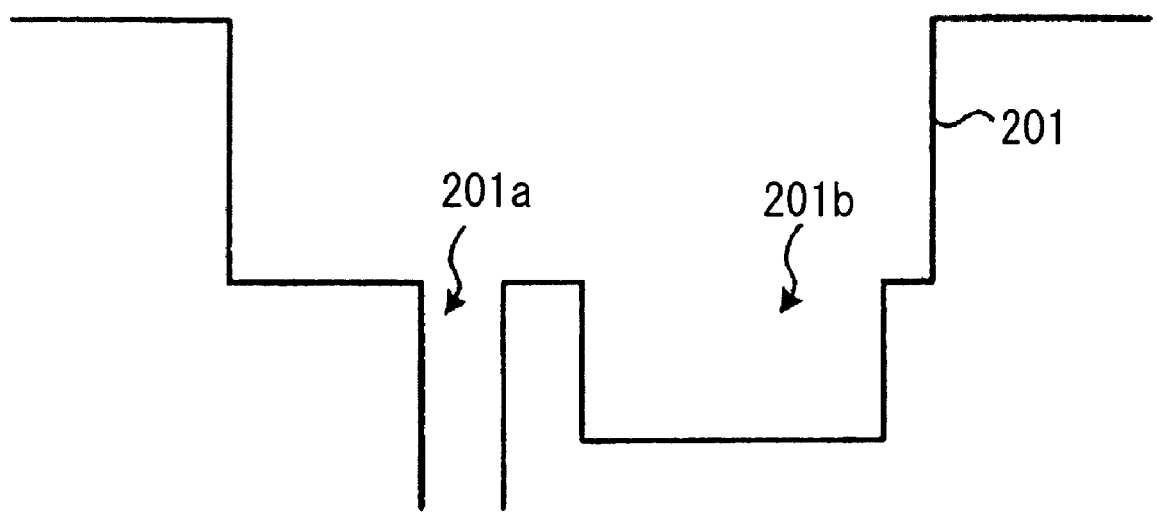
FIG. 5 is a sectional view of the trap aperture according to the embodiment.

FIG. 5 is a sectional view showing a section taken along line B-B in FIG. 4. As shown in FIGS. 4 and 5, the recess 201b is formed by depressing the bottom of the trap aperture 201 into a cylindrical shape, whereas the penetrating apertures 201a are formed piercing the bottom of the trap aperture 201 of the trap plate 103. The depth of the recess 201b is determined in accordance with the error of the thrust magnitude of the capillary needle 101, and it should desirably be set at about 2 to 3 μm by way of example.

The penetrating apertures 201a penetrate the bottom of the corresponding trap aperture 201, thereby to serve as the sole passages through which spaces on both the sides of the flat part 202 are made continuous, when the trap plate 103 is mounted in the laboratory dish 102. Therefore, when the lower side of the flat part 202 undergoes negative pressure, the cell existing on the upper side of the flat part 202 is adsorbed by the penetrating apertures 201a.

Figure 6:
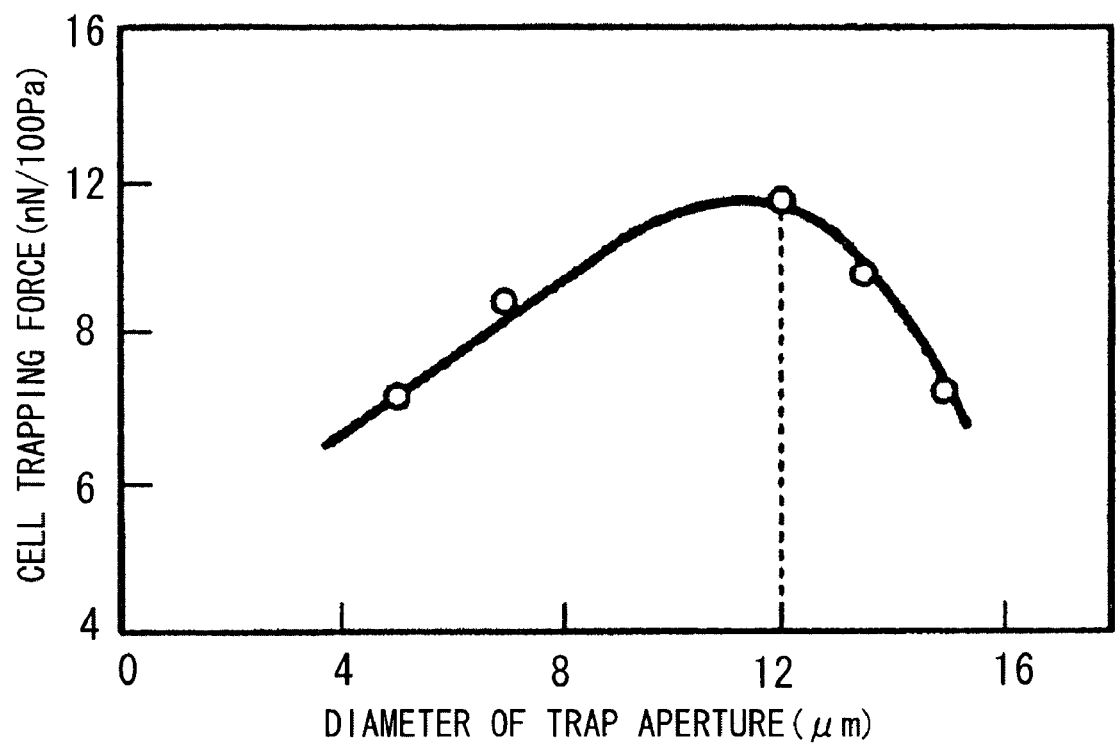
FIG. 6 is a graph showing the relationship between the diameter of the trap aperture and a cell trapping force.

FIG. 6 shows an example of the relationship between the diameter of the trap aperture 201 and a cell trapping force in the above configuration. Here, the cell trapping force was measured by setting the average diameter of the cells at 16 μm. As seen from the figure, when the diameter of the trap aperture 201 is about 12 μm, the cell trapping force becomes the maximum, and the trap plate 103 traps the cells most efficiently. The diameter 12 μm of the trap aperture 201 corresponds to 75% of the average diameter; 16 μm of the cells. It is understood that, as stated before, the diameter of the trap aperture 201 should desirably be about 70% to 80% of the diameter of the cell.

More specifically, when the diameter of the trap aperture 201 is excessively small in comparison with the cell, that part of the cell which enters the trap aperture 201 is small relative to the size of the whole cell, and the cell cannot be reliably fixed. To the contrary, when the diameter of the trap aperture 201 is excessively large in comparison with the cell, a margin appears around the cell and the whole cell enters the trap aperture 201. In this case, the cell cannot be reliably fixed.

Figure 7:
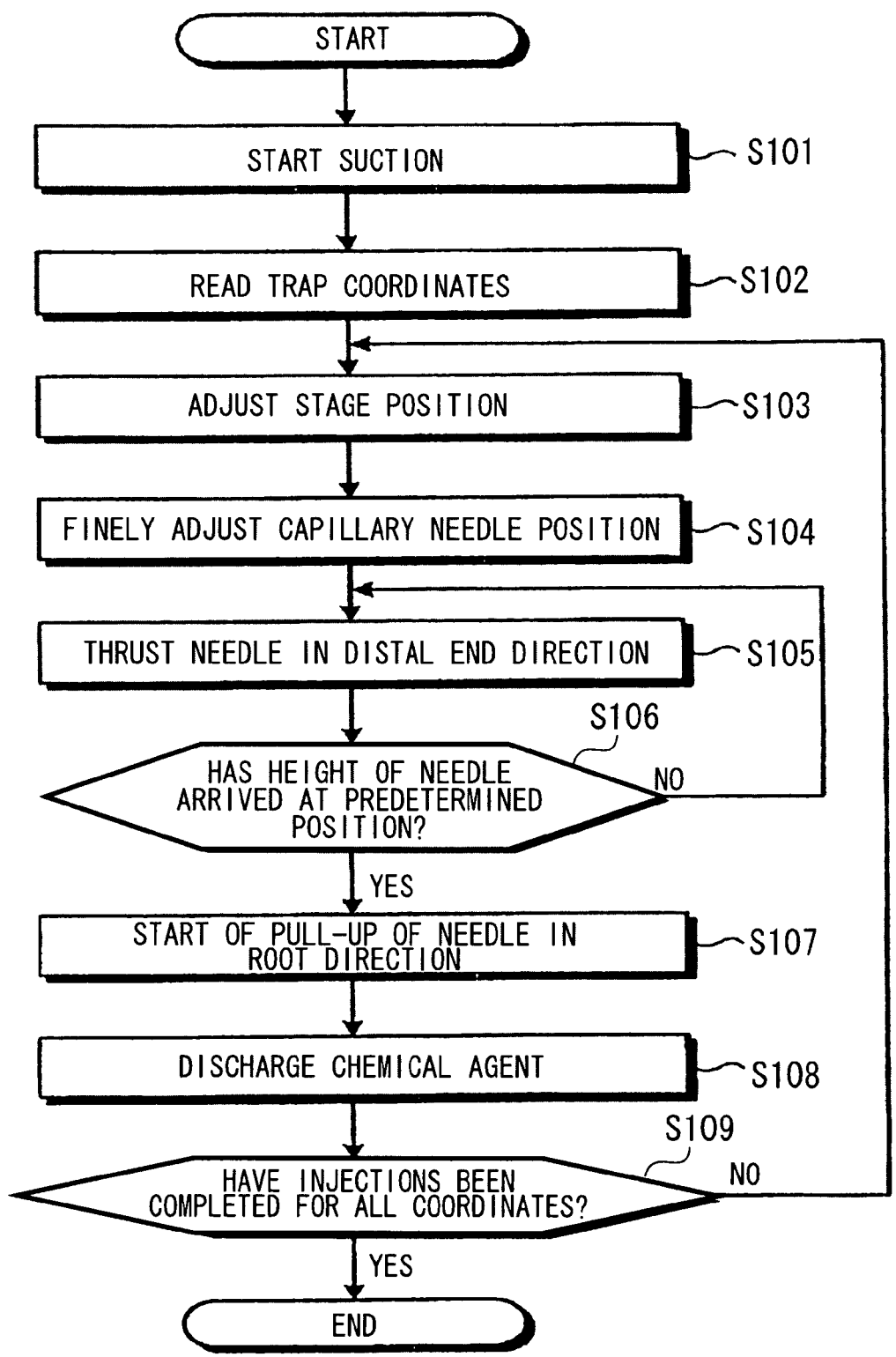
FIG. 7 is a flow chart showing an injection operation according to an embodiment.

Next, an injection operation based on the automatic microinjection apparatus 100 configured as stated above will be described with reference to a flow chart shown in FIG. 7.

In starting the injection, the trap plate 103 is mounted in the laboratory dish 102, and the laboratory dish 102 is filled up with a buffer liquid in which a plurality of cells survives. In this state, the suction of the side of the trap plate 103 near to the bottom of the laboratory dish 102 is started by the suction portion 106 (step S101). Upon the start of the suction, the side of the trap plate 103 near to the bottom of the laboratory dish 102 becomes a negative pressure, and the buffer liquid in the laboratory dish 102 passes through the penetrating apertures 201a of the trap plate 103 and flows onto the side of the trap plate 103 near to the bottom of the laboratory dish 102. In consequence, the cells in the buffer liquid are adsorbed on the penetrating apertures 201a and are trapped by the trap apertures 201. Thus, the cells are fixed to the coordinates of the trap apertures 201 of the trap plate 103.

On the other hand, the coordinates of all the trap apertures 201 are read from the trap coordinate storage portion 109 by the control portion 110 (step S102). Since the cells are trapped on the trap apertures 201 as stated above, the coordinates of the trap apertures 201 are no other than trap coordinates at which the cells are trapped. When the trap coordinates have been read by the control portion 110, any of the trap coordinates is notified from the control portion 110 to the stage movement mechanism portion 107, and the stage movement mechanism portion 107 is instructed to move the notified trap coordinates to the position of a subject for the injection. That is, the stage movement mechanism portion 107 is requested to adjust the position of the stage 104 in order that the trap coordinates at which the cell is trapped may be located perpendicularly below the illuminator 105 and perpendicularly above the lens of the inverted microscope 113.

In addition, the position of the stage 104 is adjusted by the stage movement mechanism portion 107 (step S103). That is, the stage 104 is moved on the horizontal surface by the stage movement mechanism portion 107, whereby the laboratory dish 102 as well as the trap plate 103 on the stage 104 takes the position instructed by the control portion 110. Besides, the position of the capillary needle 101 in a horizontal direction is finely adjusted by the capillary-needle movement mechanism portion 108 in order that the distal end of the capillary needle 101 may be located perpendicularly below the illuminator 105 at the discharge of a chemical agent (step S104).

Figure 8:
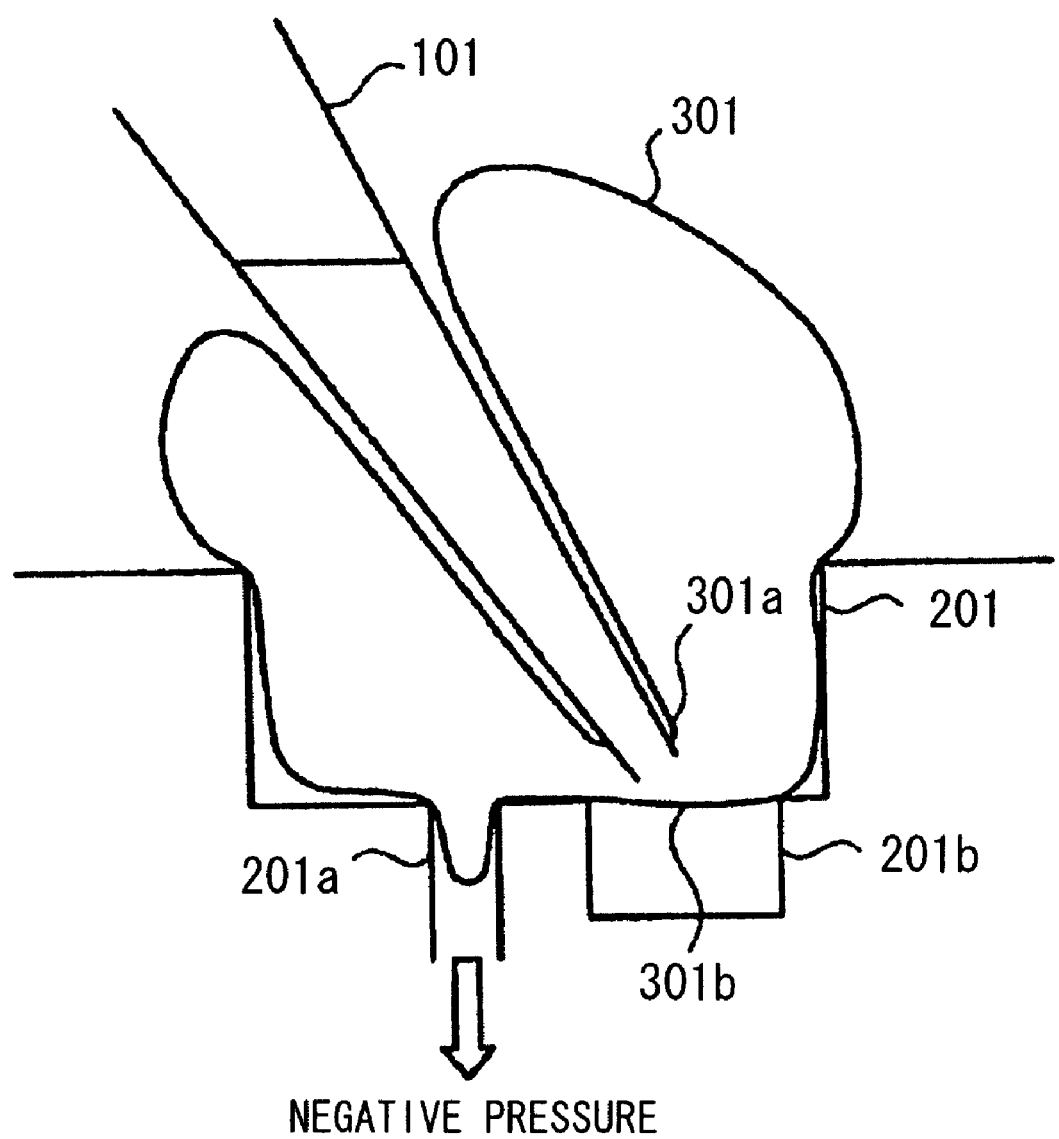
FIG. 8 is a sectional view for explaining the thrust of a capillary needle according to an embodiment.

When the horizontal positions of the stage 104 and the capillary needle 101 have been adjusted, the distal end of the capillary needle 101 is thrust in the lengthwise direction of the needle by the capillary-needle movement mechanism portion 108 (step S105). The cell is trapped by the trap aperture 201 of the trap plate 103 on the extension line of the capillary needle 101 in the lengthwise direction thereof. Accordingly, when the capillary needle 101 is thrust, its distal end touches the cell in due course. That is, the distal end of the capillary needle 101 presses the cell membrane of the cell until it pierces the upside cell membrane 301a of the cell 301 as shown in FIG. 8.

On this occasion, the upside cell membrane 301a of the cell 301 stretches with the thrust of the capillary needle 101 because of its high flexibility. Here, when the upside cell membrane 301a has stretched enough that it touches the downside cell membrane 301b of the cell 301, the cell membrane is essentially doubled and increases in strength in the vicinity of the distal end of the capillary needle 101. Thus, the stretch of the upside cell membrane 301a is suppressed, and the distal end of the capillary needle 101 pierces the upside cell membrane 301a. That is, the downside cell membrane 301b supports the upside cell membrane 301a, whereby the capillary needle 101 can pierce the upside cell membrane 301a.

Figure 10:
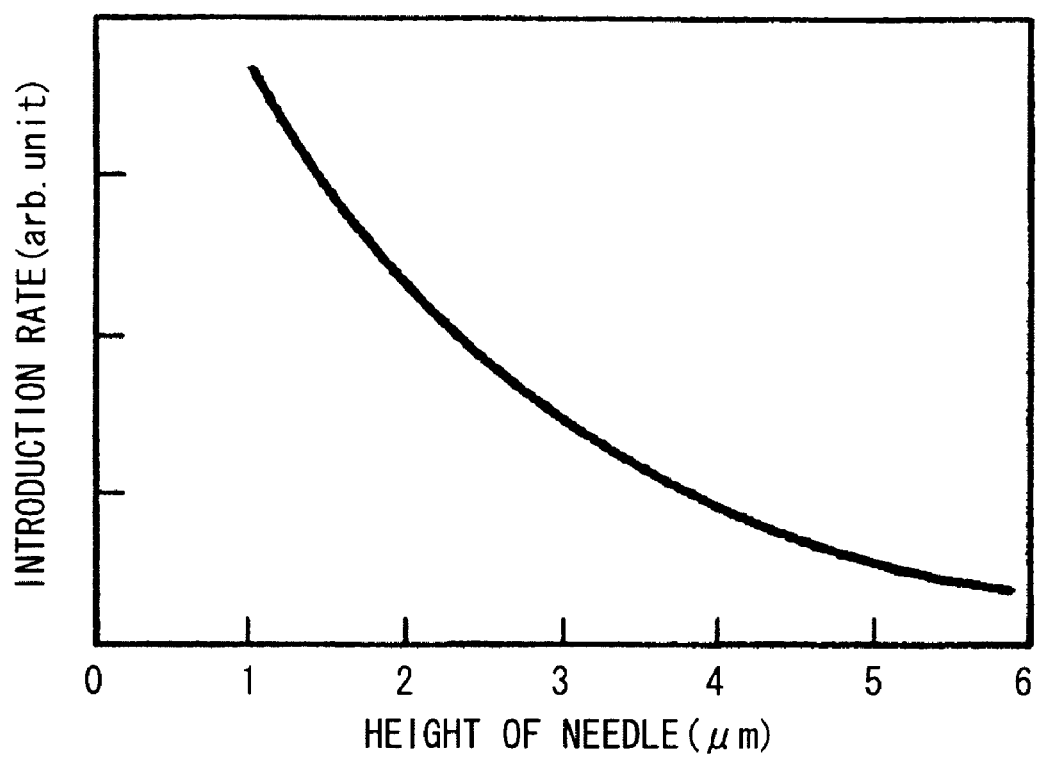
FIG. 10 is a graph showing the relationship between the height of a needle and the introduction rate of a chemical agent.

In order for the capillary needle 101 to pierce the upside cell membrane 301a in this manner, whether or not the distal end of the capillary needle 101 has arrived at a predetermined height from the bottom of the trap aperture 201 is judged by the capillary-needle movement mechanism portion 108 during the thrust of the capillary needle 101 (step S106). In general, as shown in FIG. 10, the introduction rate of the chemical agent becomes large when the height of the distal end of the capillary needle 101 arrives at about 1 μm. It is therefore considered that, when the capillary needle 101 is thrust until the distance between the distal end of the capillary needle 101 and the bottom of the trap aperture 201 becomes about 1 μm, the distal end of the capillary needle 101 will pierce the upside cell membrane 301a. Accordingly, whether or not the distal end of the capillary needle 101 has arrived at a height of, for example, 1 μm from the bottom of the trap aperture 201 is judged by the capillary-needle movement mechanism portion 108.

When the distal end of the capillary needle 101 has consequently arrived at the predetermined position (step S106: "Yes"), the capillary needle 101 begins to be pulled up onto the root side thereof in the lengthwise direction thereof by the capillary-needle movement mechanism portion 108 this time (step S107). At this stage, the chemical agent is not discharged from the distal end of the capillary needle 101 yet, and the upside cell membrane 301a has merely been broken by the distal end of the capillary needle 101. Since, however, the upside cell membrane 301a has been broken, a situation where the chemical agent fails to be injected into the cell on account of the stretch of the upside cell membrane 301a has been avoided at this stage.

In addition, during the pull-up of the capillary needle 101, the displacement of the capillary needle 101 in the lengthwise direction thereof is notified from the capillary-needle movement mechanism portion 108 to the control portion 110. When the distal end of the capillary needle 101 has been pulled up to the vicinity of the center of the cell, the discharge mechanism portion 111 is instructed to discharge the chemical agent, by the control portion 110. In other words, at a timing at which the capillary needle 101 has been pulled up to a predetermined height after being thrust to the maximum, the instruction of discharging the chemical agent is given to the discharge mechanism portion 111 by the control portion 110.

Figure 9:
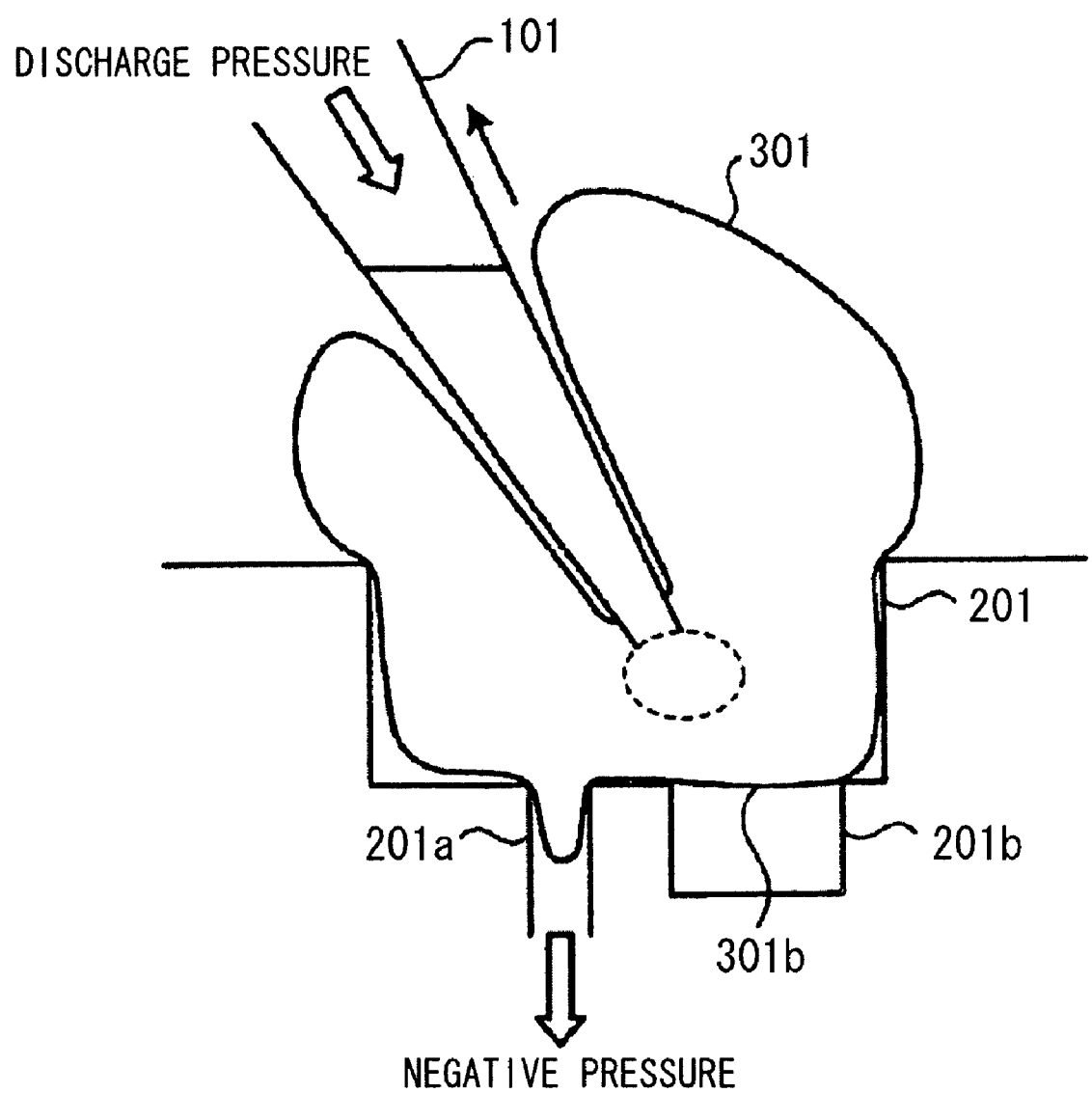
FIG. 9 is a sectional view showing withdrawal of the capillary needle subsequent to FIG. 8.

Subsequently, a discharge pressure is added to the interior of the capillary needle 101 by the discharge mechanism portion 111, and the chemical agent is discharged from the distal end of the capillary needle 101 (step S108). On this occasion, the distal end of the capillary needle 101 has been pulled up to the vicinity of the center of the cell. As shown in FIG. 9, therefore, a space sufficient for injecting the chemical agent thereinto is defined between the distal end of the capillary needle 101 and the downside cell membrane 301b. Accordingly, the chemical agent discharged from the distal end of the capillary needle 101 is reliably injected into the cell without flowing over the cell.

When the capillary needle 101 has been pulled up to its initial position after the discharge of the chemical agent from the distal end of this capillary needle 101, whether or not injections have been completed for all the trap coordinates fetched from the trap coordinate storage portion 109 is judged by the control portion 110 (step S109). In the existence of the trap coordinates for which the injection has not been completed yet (step S109: "No"), the process is repeated from the movement of the stage 104 based on the stage movement mechanism portion 107. In this way, the injections into the cells trapped at all the trap coordinates are completed.

Meanwhile, in thrusting the capillary needle 101 as stated above, the distal end approaches to about 1 μm from the bottom of the trap aperture 201. It is therefore considered that, when an error is involved in the control based on the capillary-needle movement mechanism portion 108, the distal end of the capillary needle 101 will arrive at the level of the bottom of the trap aperture 201 comparatively frequently. In this embodiment, however, the recess 201b is provided on the extension line of the capillary needle 101 in the lengthwise direction thereof in the bottom of the trap aperture 201, and hence, the distal end does not touch the bottom of the trap aperture 201 even when the capillary needle 101 is excessively thrust.

Figure 11:
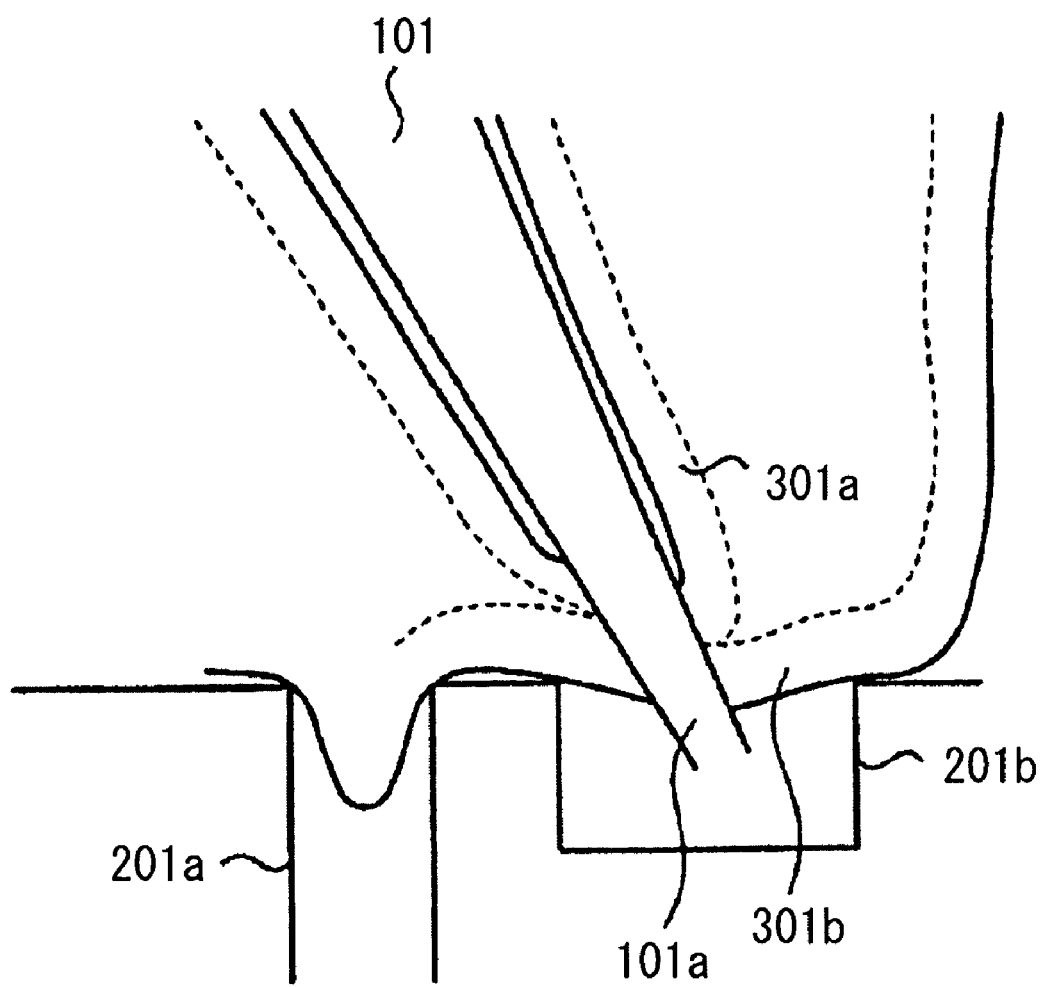
FIG. 11 is an enlarged view showing the vicinity of the distal end of the capillary needle during the injection according to the embodiment.

More specifically, even in a case as shown in FIG. 11 where the distal end 101a of the capillary needle 101 pierces, not only the upside cell membrane 301a, but also the downside cell membrane 301b, on account of the error of the thrust of the capillary needle 101, and where it arrives at the level of the bottom of the trap aperture 201, it merely enters the recess 201b and does not touch the trap plate 103. Therefore, the distal end 101a of the capillary needle 101 is not damaged.

Moreover, in this embodiment, the chemical agent is not discharged at a timing at which the capillary needle 101 has been thrust to the maximum, but it is discharged during the pull-up of the capillary needle 101. Accordingly, even when the distal end 101a of the capillary needle 101 has fallen into the state shown in FIG. 11, the chemical agent is not discharged in the state where the distal end 101a of the capillary needle 101 exists outside the cell, and it is reliably discharged within the cell.

Figure 12:
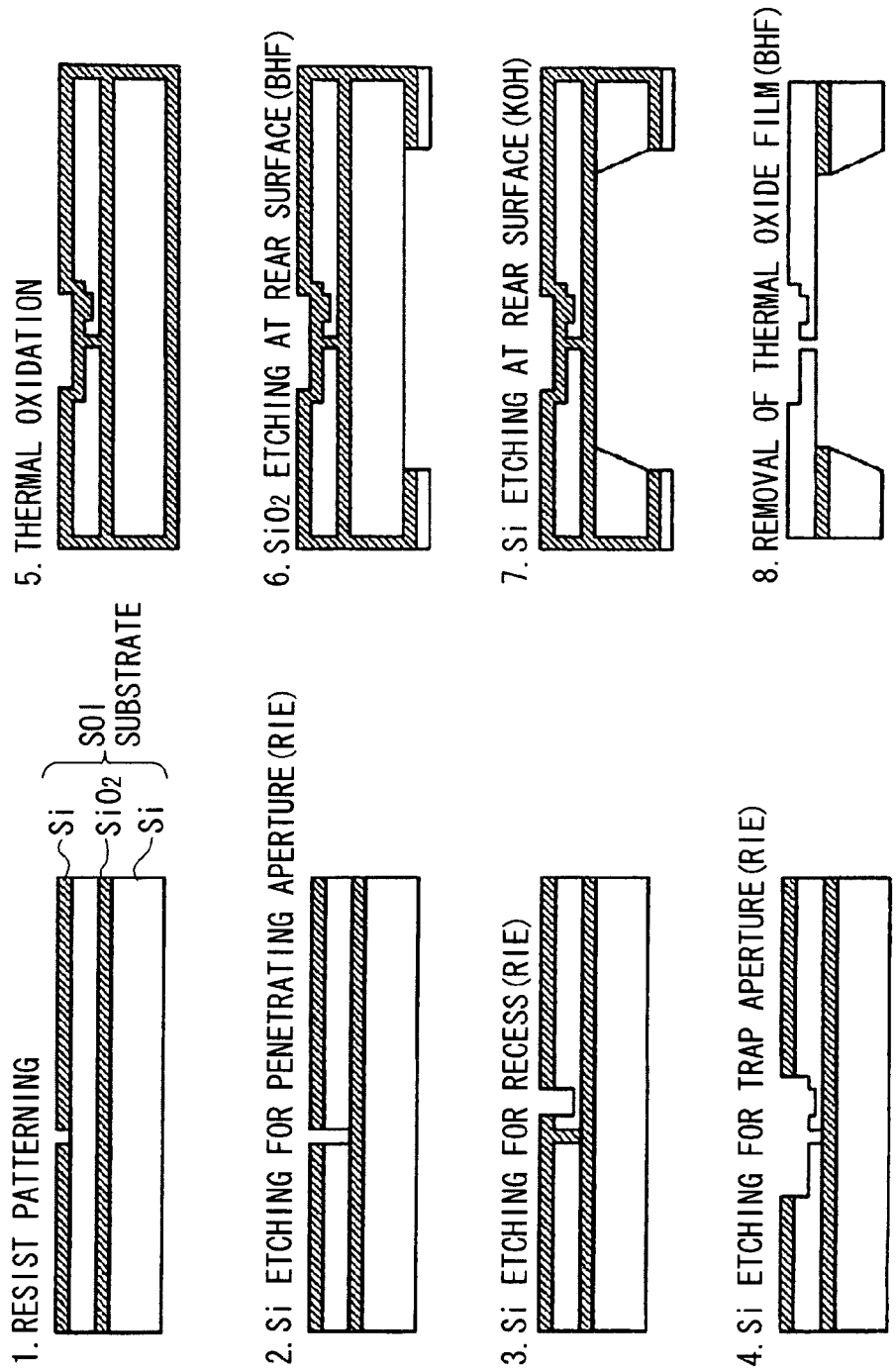
FIG. 12 is a flow sheet showing a manufacturing method for the trap plate according to the embodiment.
Figure 13:
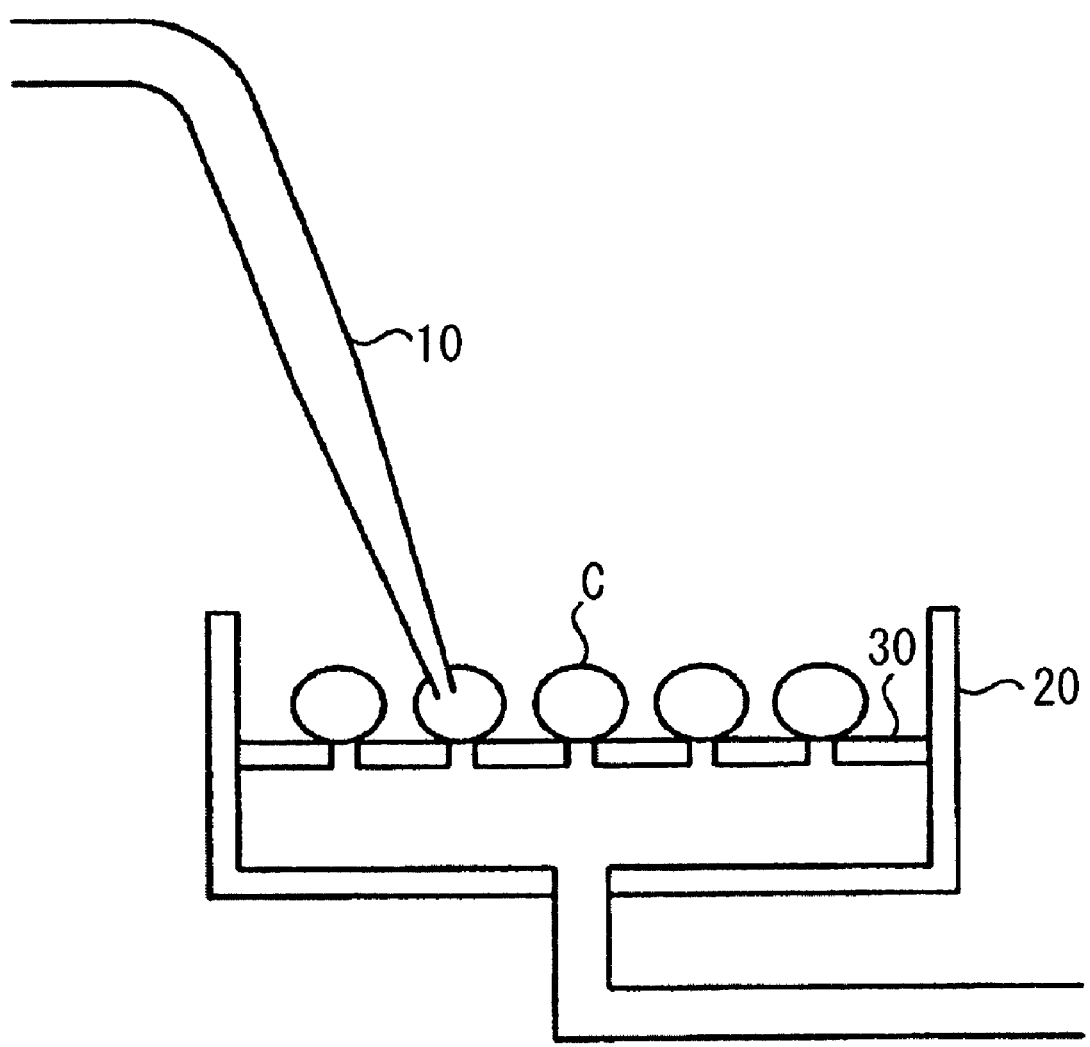
FIG. 13 is a sectional view showing an example of a cell trapping method in an injection operation.
Figure 14:
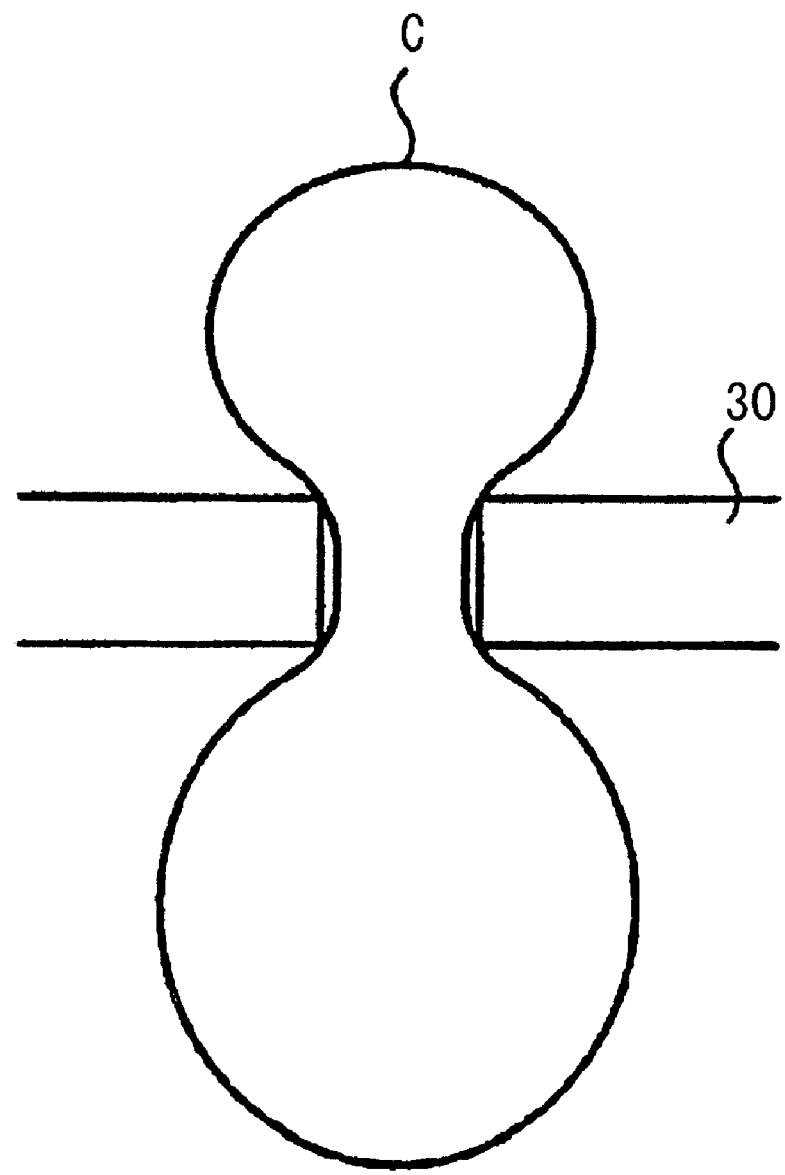
FIG. 14 is a sectional view showing an example of a trapped cell.
Figure 15:
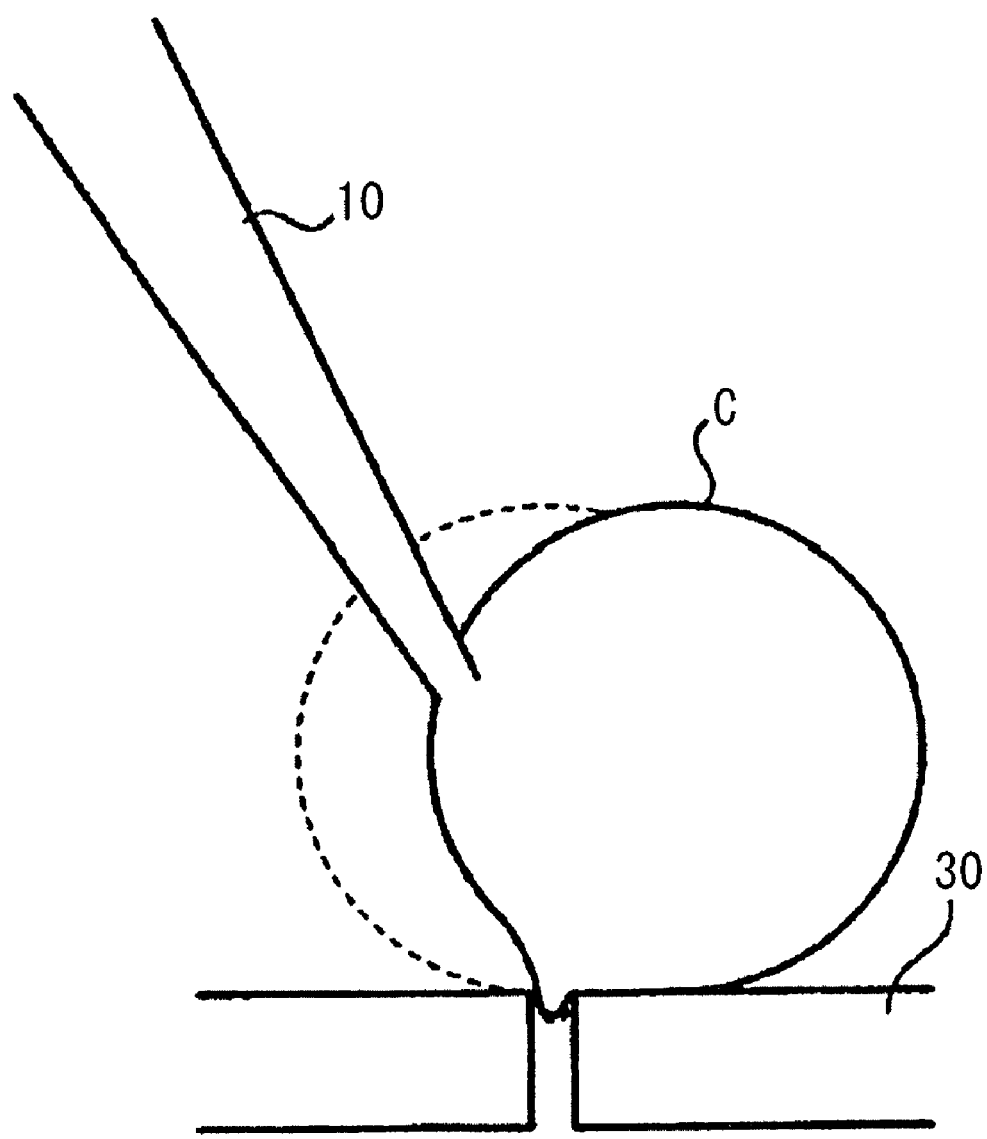
FIG. 15 is a sectional view showing another example of a trapped cell.
Figure 16:
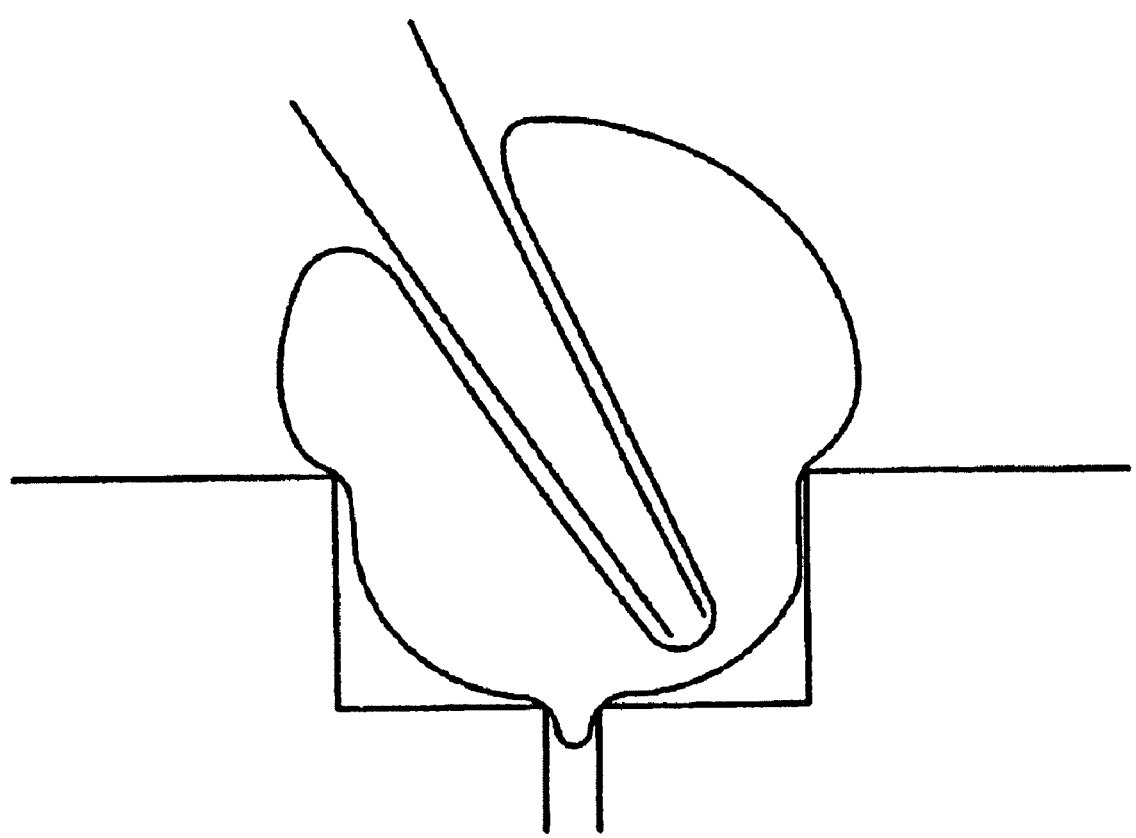
FIG. 16 is a sectional view showing the shape of a cell during the injection.

Next, a manufacturing method for the trap plate 103 according to this embodiment will be described with reference to FIG. 12. The figures shows the manufacturing steps 1 to 8 of the trap plate 103.

The trap plate 103 is manufactured using an SOI (Silicon On Insulator) substrate. First, the shape of each trap aperture 201 is transferred onto the SOI substrate by resist patterning (manufacturing step 1). In addition, each penetrating aperture 201a is formed in an active silicon layer having a thickness of about 10 μm, by RIE (Reactive Ion Etching) (manufacturing step 2). Likewise, the cylindrical shapes of the whole recess 201b and the whole trap aperture 201 by the RIE (manufacturing steps 3 and 4) are formed. In this way, the shape of the trap aperture 201 of the trap plate 103 is adjusted.

In addition, the whole SOI substrate formed with the trap apertures 201 is protected with a silicon oxide film by thermal oxidation (manufacturing step 5). Thereafter, that part of the trap plate 103 which corresponds to each leg 203 is masked, and that part of the silicon oxide film which underlies the flat part 202 is etched with buffer fluoric acid (BHF) (manufacturing step 6). Subsequently, the active silicon layer underlying the flat part 202 is anisotropically etched with a potassium hydroxide (KOH) solution (manufacturing step 7). Finally, the whole silicon oxide film is removed with the buffer fluoric acid (BHF), and the trap plate 103 is finished (manufacturing step 8).

In this manner, the trap plate 103 according to this embodiment has the trap apertures 201 etched by the RIE, so that the minute penetrating apertures 201a and recesses 201b, etc. are precisely formed. As a result, even in a case where the capillary needle 101 has been excessively thrust, the distal end thereof can be reliably protected by the recess 201b formed at a precise position.

As described above, according to this embodiment, a chemical agent is discharged while a capillary needle is being pulled up after it has been thrust to the maximum, and that part of each trap aperture for trapping a cell at which the distal end of the capillary needle arrives is formed with a recess beforehand. Therefore, even when the distance between the capillary needle thrust to the maximum and the bottom of the trap aperture is set small so as to reliably break a cell membrane, the distal end of the capillary needle merely enters the recess and is not damaged, and the chemical agent can be discharged at a timing at which a space in which the chemical agent is injected into the cell has been formed. As a result, the chemical agent can be reliably injected into the cell, and the distal end of the capillary needle can be protected.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A microinjection apparatus for injecting a substance into a cell, comprising:
　a trap plate which traps at least one cell, so as to fix a position thereof;
　a capillary needle which injects the substance into the cell trapped by the trap plate;
　a movement mechanism portion which moves a distal end of the capillary needle in a lengthwise direction of the capillary needle into a first position in the cell, and which thereafter withdraws the capillary needle in the lengthwise direction thereof to a second, withdrawn position within the cell; and a discharge control portion which discharges the substance from the distal end of the capillary needle when the capillary needle has been withdrawn to the second position by the movement mechanism portion.

2. The microinjection apparatus as recited in claim 1, wherein the trap plate is formed with a plurality of trap apertures for trapping respective cells, each at predetermined coordinates.

3. The microinjection apparatus as recited in claim 2, wherein each of the trap apertures has a circumference, and each of the trap apertures has a diameter which corresponds to 70% to 80% of a diameter of the cell.

4. The microinjection apparatus as recited in claim 1, wherein:
   the trap plate includes:
      a flat part which traps the least one cell on a first surface thereof; and
      a projection which supports the flat part so as to define a sealed space on a second, opposite surface of the flat part; and
   the flat part includes a plurality of trap apertures, each of which has a cylindrical shape.

5. The microinjection apparatus as recruited in claim 4, wherein each of the trap apertures is formed with a penetrating aperture which opens to the first and second surfaces.

6. The microinjection apparatus as recited in claim 5, wherein a diameter of the penetrating aperture is 1 to 2 μm, or it corresponds to 10% to 20% of a diameter of the cell.

7. The microinjection apparatus as recited in claim 4, wherein each of the trap apertures is formed with a recess formed into a bottom of the trap aperture, and the recess has a bottom near a position of a distal end of the capillary needle moved by the movement mechanism portion to a maximum movement position.

8. The microinjection apparatus as recited in claim 7, wherein the recess has a diameter of 3 to 4 μm and which has a depth of 2 to 3 μm.

9. A trap plate for trapping at least one cell in a buffer liquid and for fixing a position thereof, in order to inject a substance into the cell, comprising:
   a trap aperture formed into the top plate;
   at least one penetrating aperture in the trap aperture which penetrates through the trap plate for trapping the at least one cell, and whose diameter is relatively smaller than a diameter of the cell; and
   a closed bottom recess formed into a bottom of the trap aperture near a position of a front end of a capillary needle for injecting the substance into the at least one trapped cell.

10. A microinjection method in a microinjection apparatus including a trap plate which traps at least one cell, so as to fix a position thereof, and a capillary needle which injects a substance into the cell trapped by the trap plate, comprising:
   moving a distal end of the capillary needle in a lengthwise direction of the capillary needle to a first position in the cell;
   withdrawing the capillary needle in the lengthwise direction, after the moving step to a second, withdrawn position; and
   discharging the substance from the distal end of the capillary needle, when the capillary needle has been withdrawn to the second position by the withdrawing step.

11. The microinjection apparatus as recited in claim 7, wherein the lengthwise direction of the capillary needle defines a predetermined angle relative to a vertical direction, so that the recess is formed at a position spaced from a center of the respective trap aperture.

12. The trap plate as recited in claim 9, wherein the lengthwise direction of the capillary needle defines a predetermined angle relative to a vertical direction, so that the recess is formed at a position spaced from a center of the penetrating aperture.

13. The microinjection method as recited in claim 10, wherein a plurality of cells is trapped on the trap plate and the moving, withdrawing and discharging steps are preformed on each of the cells by moving the trap plate relative to the capillary needle.

14. The microinjection method as recited in claim 13, wherein the position of each cell is stored prior to moving the trap plate.

* * * * *

UNITED STATES PATENT AND TRADEMARK OFFICE
CERTIFICATE OF CORRECTION

| | |
|---|---|
| PATENT NO. | : 7,897,395 B2 |
| APPLICATION NO. | : 12/081994 |
| DATED | : March 1, 2011 |
| INVENTOR(S) | : Akio Ito et al. |

It is certified that error appears in the above-identified patent and that said Letters Patent is hereby corrected as shown below:

Column 11, Line 23 in Claim 5, delete "recruited" and insert -- recited --, therefor.

Column 11, Line 36 in Claim 8, after "and" delete "which has".

Signed and Sealed this
Third Day of May, 2011

David J. Kappos
*Director of the United States Patent and Trademark Office*